(12) United States Patent
Maxfield et al.

(10) Patent No.: US 7,725,179 B2
(45) Date of Patent: May 25, 2010

(54) CATHETER, IN PARTICULAR FOR INSERTION OF HEART-PACEMAKER-OR ICD-ELECTRODES INTO A PATIENT'BODY

(75) Inventors: Michelle Maxfield, Berlin (DE); Erhard Flach, Berlin (DE); Wolfgand Geistert, Rheinfelden (DE)

(73) Assignee: Biotronik CRM Patent AG, Baar (CH)

( * ) Notice: Subject to any disclaimer, the term of this patent is extended or adjusted under 35 U.S.C. 154(b) by 861 days.

(21) Appl. No.: 11/253,790

(22) Filed: Oct. 20, 2005

(65) Prior Publication Data

US 2006/0095106 A1 May 4, 2006

(30) Foreign Application Priority Data

Oct. 20, 2004 (DE) .................... 10 2004 051 211

(51) Int. Cl.
*A61M 25/01* (2006.01)
(52) U.S. Cl. .......................................... 607/4
(58) Field of Classification Search .......... 607/122, 607/4; 604/523, 524, 525, 526, 527
See application file for complete search history.

(56) References Cited

U.S. PATENT DOCUMENTS

| 5,507,751 | A |   | 4/1996 | Goode et al. |
| 5,743,876 | A |   | 4/1998 | Swanson et al. |
| 5,782,811 | A | * | 7/1998 | Samson et al. ............ 604/527 |
| 6,159,198 | A |   | 12/2000 | Gardeski et al. |
| 6,251,092 | B1 |   | 6/2001 | Qin et al. |
| 6,402,781 | B1 |   | 6/2002 | Langberg et al. |
| 6,549,812 | B1 |   | 4/2003 | Smits |
| 6,556,873 | B1 |   | 4/2003 | Smits |
| 2004/0167437 | A1 |   | 8/2004 | Sharrow et al. |
| 2005/0222678 | A1 | * | 10/2005 | Lashinski et al. .......... 623/2.11 |
| 2006/0095106 | A1 | * | 5/2006 | Maxfield et al. ............ 607/122 |

FOREIGN PATENT DOCUMENTS

| DE | 33 82 818 T2 | 7/1998 |
| DE | 297 02 413 U1 | 7/1998 |
| DE | 694 17 206 T2 | 8/1999 |
| DE | 100 58 105 A1 | 7/2001 |
| DE | 100 58 106 A1 | 7/2001 |
| DE | 101 03 955 A1 | 11/2001 |
| EP | 0 608 853 A2 | 8/1994 |
| EP | 0 655 257 A2 | 5/1995 |
| EP | 0 790 066 A2 | 8/1997 |
| EP | 0 898 481 B1 | 3/1999 |
| EP | 1 457 224 A1 | 9/2004 |
| JP | 20011299923 | 10/2001 |
| WO | WO 96/38193 A1 | 12/1996 |
| WO | WO 99/33509 A1 | 7/1999 |
| WO | WO 99/64098 A1 | 12/1999 |
| WO | WO 03/059429 A2 | 7/2003 |

* cited by examiner

*Primary Examiner*—Carl H Layno
*Assistant Examiner*—Michael D'Abreu
(74) *Attorney, Agent, or Firm*—Browdy and Neimark, PLLC

(57) ABSTRACT

A catheter, in particular for insertion of heart-pacemaker- or ICD-electrodes into a patient's body, comprises a catheter wall and a reinforcement therein for stabilization of the catheter. The reinforcement is a profile element which is adjusted to the desired mechanical properties of the catheter in the axial and peripheral direction thereof.

10 Claims, 2 Drawing Sheets

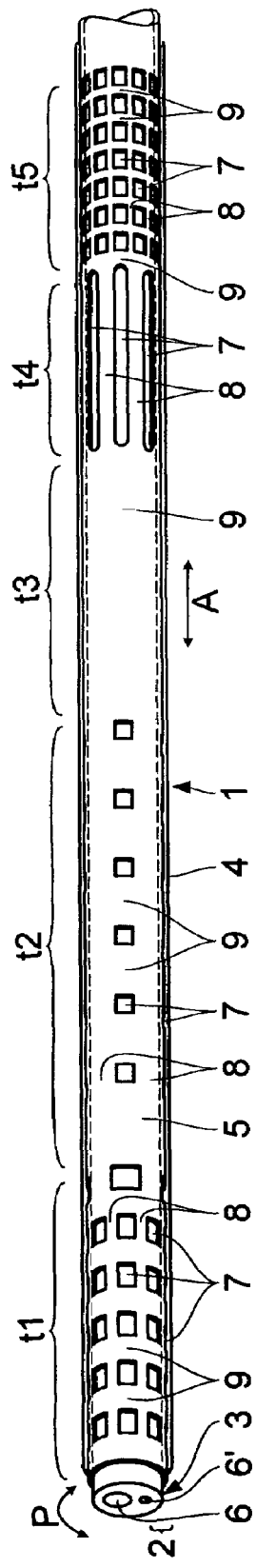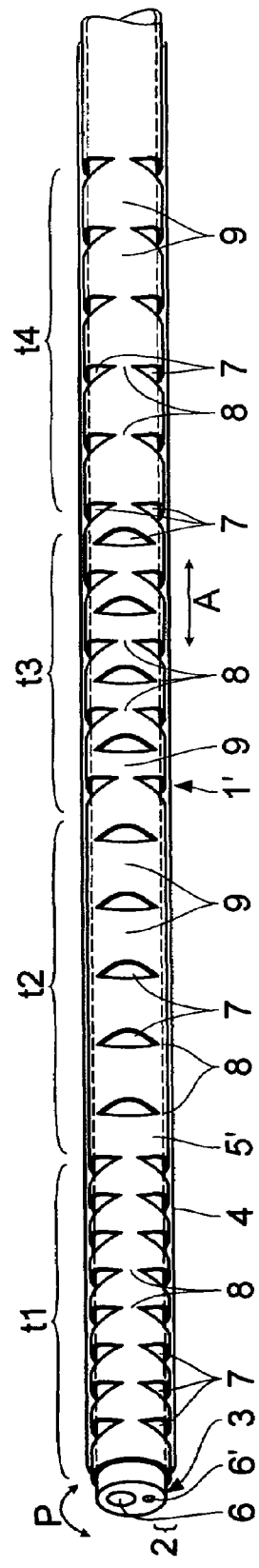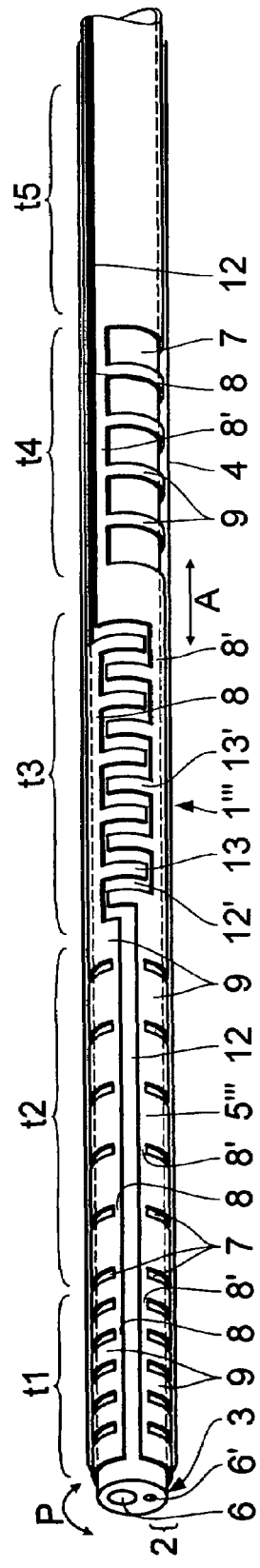

CATHETER, IN PARTICULAR FOR INSERTION OF HEART-PACEMAKER-OR ICD-ELECTRODES INTO A PATIENT'BODY

FIELD OF THE INVENTION

The invention relates to a catheter, in particular for insertion of heart-pacemaker- or ICD-(=implantible cardioverter defibrillator)-electrodes into a patient's body, comprising a catheter wall and a reinforcement therein.

BACKGROUND OF THE INVENTION

Catheters of the generic type are known to comprise at least one lumen that is defined by the catheter wall and serves for guidance of the electrode that must be inserted in a patient's body after insertion of the catheter. Another lumen may for example serve for displacement of the catheter by a guide wire that has been applied in advance in a patient's body or for equipment of the catheter tip with a wire pull.

Catheters of the generic type are also known to have a slit- or tear-open catheter wall so that they can easily be removed from a patient's body once the electrode has been placed. EP 0 655 257 A2 shows a catheter of that type, disclosing a catheter wall with a weakening in the form of a perforation.

A current problem in these catheters resides in the torsional and buckling strength of the catheter shank and the susceptibility thereof to compression, in particular when the catheter must be bent around a small radius, which is for example the case during insertion into the arteria subclavia.

For solving these problems, the prior art teaches to provide the catheter wall with reinforcements, by the aid of which to stabilize a catheter's torsional and/or buckling strength and to counteract any undesired compression. In this context, EP 0 898 481 B1, U.S. Pat. No. 6,159,198 A and WO 99/33509 A1 disclose to place reinforcement fibers into the catheter wall. They may be individual fibers as shown in WO 99/33509 A1 and EP 0 898 481 B1, or a meshed hose as taught in U.S. Pat. No. 6,159,198 A.

Although the inserted fibers fundamentally help in the task of reinforcement, they pose some problems in particular in the manufacture of a catheter. Fundamentally, placing fiber reinforcements as a mesh or strand structure in a hose configuration is a customary method of production, however, these fiber reinforcements are hard to adapt to certain desired properties in the axial and peripheral direction. This applies in particular when the catheter is intended to be weakened for a tear line to be provided. In this context, EP 0 898 481 B1 (mentioned above) teaches a perforation line which serves for the reinforcement fibers that extend in the peripheral direction along the catheter wall to rip open only initially. Putting this step, which is outlined diagrammatically, into practice will need considerable requirements in terms of manufacture. This applies all the more to the reinforcement fibers of strongly flatly rectangular cross-sectional shape which are mentioned in the above document and which must be expected to be severed when the perforation lines are too deep.

SUMMARY OF THE INVENTION

Proceeding from these prior art problems, it is an object of the invention to improve a catheter of the species for obtaining, in a simple way, mechanical properties that vary in the axial as well as the peripheral direction such as torsional, bending and buckling strength, compressibility, flexibility and the ability of splitting.

This object is achieved by the invention, fundamentally and distinctly providing that the reinforcement is embodied as a profile element which conforms to desired mechanical properties of the catheter in the axial and peripheral direction thereof. For instance, a varying wall thickness of the profile element can help achieve varying flexibility, buckling strength and compression strength along the length of the catheter. By advantage, there is no longer any need of uniting and gluing or welding together various catheter-shank pieces so as to obtain varying properties in the axial and/or peripheral direction—which also constitutes prior art. Ability of the catheter to be slit can for example be achieved by constricting the wall thickness of the profile element in the peripheral direction.

Further features, details and advantages of the invention will become apparent from the ensuing description of exemplary embodiments, taken in conjunction with the drawing.

BRIEF DESCRIPTION OF THE DRAWING

FIG. 1 is a highly diagrammatic, sectional perspective view, partially broken away, of a first embodiment of a catheter;

FIGS. 2 to 4 are perspective views, by analogy to FIG. 1, of three other embodiments of the catheter.

DESCRIPTION OF THE PREFERRED EMBODIMENT

Figure 3:
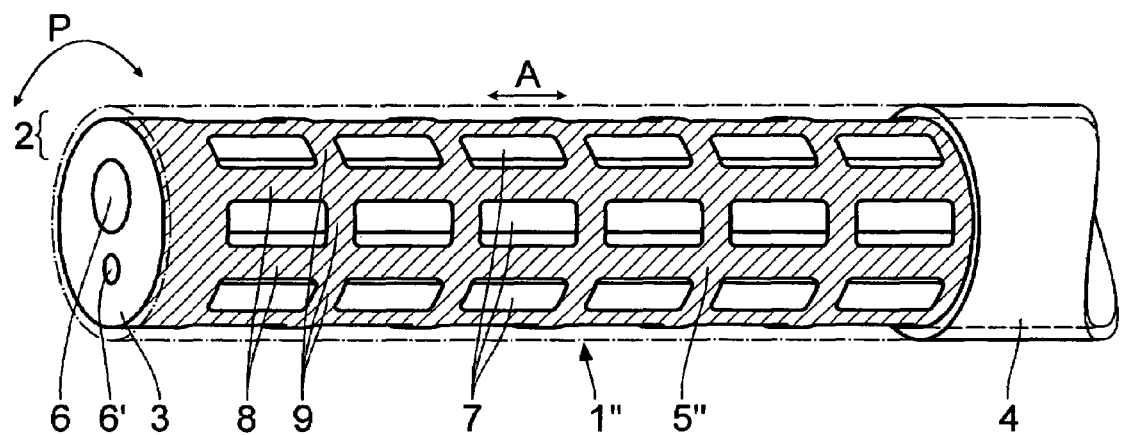

The catheter 1 seen in FIG. 1 comprises a catheter wall 2 which, radially from the inside to the outside, is comprised of an internal hose 3, an external hose 4 and an intermediate profile element 5. Two lumens 6, 6' are provided in the internal hose 3, which extend from the proximal to the distal end (not shown) of the catheter 1 and through which to push for example a heart-pacemaker electrode and a pull wire. The internal and external hoses 3, 4 consist of extruded elastomeric material as is customary for use in medical hoses and tubes.

In the exemplary embodiment seen in FIG. 1, the profile element 5 has the basic shape of a longitudinal cylindrical lattice profile element, the illustrated area of which is divided into sectional lengths t1, t2, t3, t4 and t5 of varying profile patterns. Fundamentally, axial ribs 8 that run in the axial direction A and peripheral ribs 9 that run in the peripheral direction P are formed by holes 7 in the jacket wall of the element 5. As roughly outlined in the drawing, by variation of the jacket-wall thickness of the lattice profile element 5 and in particular of the size of the holes 7 and/or the cross-sectional dimensions of the axial and peripheral ribs 8, the various sectional lengths t1 to t5 can be designed for the profile element to conform to the desired mechanical properties of the catheter. For example, by enlarging each hole 7 in a direction towards the distal end and by reducing the widths of the axial and peripheral ribs 8, 9, the torsional and bending resistance of the catheter 1 along the sectional length t1 can be distinctly reduced as compared to the sectional length t2. Furthermore, very thin and short peripheral ribs 9 can be left between two rows of holes 7—which is not shown explicitly—which then constitute a predetermined breaking point for the catheter 1 to be ripped open and withdrawn from the inserted electrode. A "hybrid" of axial and peripheral ribs can be put into practice by inclined diagonal ribs.

The sectional length t3 of the profile element does not have any holes 7 i.e., it is cylindrical, this offering excellent compression strength.

An area of oblong holes 7 ensues on the sectional length t4, the oblong holes 7 forming between them axial ribs 8 which are parallel to one another. In this area, the profile element 5 is comparatively susceptible to torsion i.e., it can easily be intertwisted.

The adjoining sectional length t5 exhibits a pattern in the form of a narrow lattice of axial and peripheral ribs 8, 9, rendering this part of the profile element 5 very flexible, but torsionally stable.

There are various ways of manufacturing the lattice profile element 5 of FIG. 1, laser cutting, punching or etching from a hose, tube or flat material, such as a piece of film, being conceivable. In this latter case, the piece of material, which has been patterned while flat, will then be rolled up and wound as a profile element for example on the internal hose 3. Manufacture in the form of an injection-molded, extruded or similarly thermally molded hose or tube is conceivable.

The above semi-finished products can be made of plastic material, such as polycarbonate, polyimide and the like, or of a metal material, such as nitinole or stainless steel.

After manufacture, the lattice profile element 5 in the form of a semi-finished product can be embedded between the internal and external hoses 3, 4 by gluing, shrinking or melting. Direct injection into a single-piece hose wall is possible just as well.

In addition to the above mechanical and thermoplastic manufacturing techniques, the lattice profile element 5 can also be produced by the internal hose 3 being coated with a uv- or laser- or chemically curable plastic material by a kind of lithographic process. To this end, a mask is placed on the coating, the mask being the negative of the desired lattice pattern. By radiation or contacting with a chemical curing agent, for example by dipping or spraying, the coating of the exposed locations that are not covered by the mask cures by cross-linkage, after which the mask is withdrawn. Then the zones of the coating that have not cured can be removed by a suitable solvent and a lattice profile element 5 is obtained, having the desired hole pattern. The external hose 4 will then be shrunk, glued or extruded on to the profile element 5 with the internal hose 3.

The above job of masking can be dropped when the zones to be cured of the coating are scanned by a scanner laser or focused ultraviolet light and then cross-linked.

Finally, the profile element 1 may also be produced by the internal hose 3 being printed with a rib pattern of curable material, such as a printing paste, the material then being cured by radiation or chemical cross-linkage.

In the embodiment of the catheter 1' seen in FIG. 2, provision is again made for an internal hose 3 with two lumens 6, 6', an external hose 4 and an intermediate profile element 5'. The sectional lengths t1 to t4 thereof are provided with a pattern that deviates from the embodiment of FIG. 1. In this embodiment, the design of the profile element 5' is characterized by the catheter 1' being extraordinarily pliable at certain defined levels along these sectional lengths t1 to t4. For example, the sectional length t1 is provided with successive spandrel-type holes 7 on two sides that face away from each other, forming between themselves peripheral ribs 9 of a course of width in the shape of an hourglass. The peripheral ribs 9 are joined to one another by two opposed axial ribs 8. This configuration makes the catheter excellently pliable along the sectional length t1 in the plane of projection of FIG. 2.

Along the sectional length t2, the spandrel-type holes 7 are displaced from the holes of the sectional length t1, having a greater distance from one another. This renders the catheter rigid along this sectional length t2 in the plane of projection of FIG. 2, however excellently pliable for deflection from the plane of projection. However, owing to the greater distance of the holes 7 as compared to the sectional length t1, pliability is reduced.

Along the sectional length t3, successive holes 7 are misaligned from one another by 90° so that a kind of skewed-lattice profile element results, having inclined peripheral ribs 9 and axial ribs 8 that are interrupted in the axial direction. The 90° misalignment of successive holes 7 renders the catheter 1' flexible along this sectional length t3 in the plane of projection of FIG. 2 as well as perpendicularly thereto.

Few holes 7 are provided at a great distance from each other along the sectional length t4 so that the catheter 1' is very rigid in this area, at best possessing some minor pliability in the plane of projection of FIG. 2 (by analogy to the sectional length t1).

As regards the manufacture of the profile element 5' and incorporation thereof in the catheter structure, reference can be made to what is said in connection with FIG. 1.

In the embodiment of the catheter 1" seen in FIG. 3, the lattice structure of the profile element 5" is prepared directly in the internal hose 3. As shown, the internal hose 3 again comprises two lumens 6, 6', its surface being provided with a reinforcement in the form of a lattice structure with axial and peripheral ribs 8, 9 that are hatched in FIG. 2. Curable material is employed for the internal hose 3; it is exposed to radiation in the hatched zones of FIG. 3, thus being cured. Removal of the zones that have not been exposed to radiation can be dropped so that the component has a plane surface in spite of the integrated reinforcement. For further curing of the internal hose 3 to be prevented, and thus further reinforcement by growth of the ribs 8, 9 of the profile element 5", an external hose 4 is applied in the way described.

Figure 5:
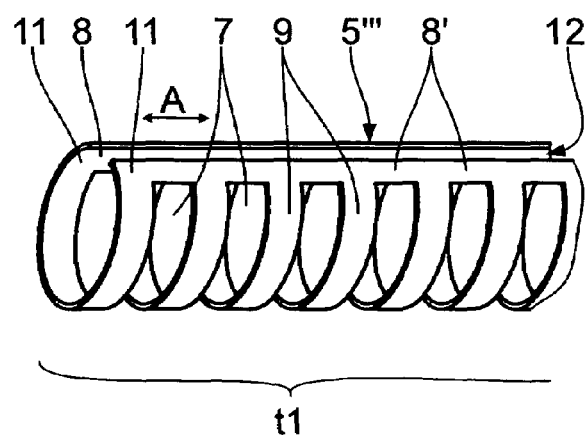
FIG. 5 is a diagrammatic perspective view of details of a profile element inserted in the catheter according to FIG. 4.

Finally, another embodiment of a catheter 1''' is illustrated in FIGS. 4 and 5. As regards the internal and external hose 3, 4, this embodiment does not differ from that of FIG. 1. In this regard, reference is made to the details there explained.

The profile element 5''' is a single piece made of hard plastic material, such as polycarbonate or polyimide, or also of thin metal material, such as stainless steel or nitinole; along the sectional lengths t1, t2 and t4, it possesses peripheral ribs 9 which extend at a distance from, and in parallel to, each other. They are partial rings, the ends 11 of which being respectively connected to each other by an axially continuous axial rib 8, 8'. A gap 12 is left between the two axial ribs 8, 8', serving in the catheter 1''' as a predetermined breaking point for the catheter 1''' to be torn open and the inserted electrode to be removed.

The holes 7 and in particular the peripheral ribs 9 are configured to vary along the sectional lengths t1 to t4 in the embodiment according to FIG. 4. The sectional length t1, which extends towards the distal end, is provided with comparatively thin peripheral ribs 9 so that the catheter is comparatively flexible there. The peripheral ribs 9 are clearly wider along the sectional length t2 that adjoins in the proximal direction, which implies a decrease in flexibility.

The axial ribs 8, 8' show a special configuration in the area of the sectional length t3 where they have projections 13 which are directed in the peripheral direction P and are displaced from one another in such a way that they intermesh, forming a meandering gap section 12'. As a result, the catheter 1''' is torsionally stable in this area.

Along the sectional length t4, comparatively thin peripheral ribs 9 are separated from one another by holes 7 which are wide in the axial direction so that the catheter is very flexible in the center plane that passes through the gap 12 there extending.

A sectional length t5 adjoins where no holes are provided, apart from the gap 12. As a result, the catheter 1''' is very rigid there.

FIG. 5 illustrates the profile element 5''' along the sectional length t1 without the internal and external hoses being illustrated.

Finally, it is emphasized that the profile elements can be made of any material compatible with MR inspection instruments and, respectively, detectable in ultrasonic or x-ray instruments.

What is claimed is:

1. A catheter, in particular for insertion of heart-pacemaker- or ICD-electrodes into a patient's body, comprising
   a catheter wall, which defines at least one lumen, said catheter wall having a longitudinal dimension and said lumen extending in the direction of the longitudinal dimension; and
   a reinforcement in an axial and peripheral direction in the catheter wall for stabilization of the catheter in torsional and/or buckling strength;
   wherein the reinforcement is a profile element which is adjusted to desired mechanical properties of the catheter in the axial and peripheral direction thereof,
   wherein, at least along one sectional length, the profile element is a lattice profile element, and
   wherein the lattice profile element comprises: peripheral ribs in a form of partial rings that extend transversely to the longitudinal dimension, each peripheral rib having two opposed ends; and two axially continuous axial ribs that extend in the direction of the longitudinal dimension and that are each connected to a respective end of each of said peripheral ribs, said axial ribs being spaced apart in a direction transverse to the longitudinal dimension such that a gap is left between the two axial ribs, serving in the catheter as a pre-determined breaking point for the catheter to be torn open and the inserted electrode to be removed.

2. A catheter according to claim 1, wherein the profile element has properties of torsional, bending and buckling strength and of compressibility and/or ability of splitting which are adjusted by variable profile patterns on varying sectional lengths.

3. A catheter according to claim 1, wherein, with a view to the properties of the catheter of torsional, bending and buckling strength and of compressibility and/or ability of slitting, the cross section of at least one of the axial and peripheral ribs is variable in at least one of the axial and peripheral direction.

4. A catheter according to claim 1, wherein the profile element is made from a piece of hose or film of metal or plastic material by cutting or etching.

5. A catheter according to claim 1, wherein the ribs of the profile element are produced by radiation-induced or chemical cross-linkage of one of a curable piece of plastic hose and of a curable coating.

6. A catheter according to claim 1, wherein the profile element is produced by a process of thermal molding, in particular by injection-molding or extrusion.

7. A catheter according claim 1, wherein the profile element is embedded, in particular by injection, in the catheter wall.

8. A catheter according to claim 1, wherein the profile element is embedded between an internal hose and an external hose of the catheter wall.

9. A catheter according to claim 1, wherein the profile element is made of one of: a hose; a tube; and a flat material that is patterned and then rolled up and wound.

10. A catheter according to claim 1, wherein the gap extends in the direction of the longitudinal dimension of said catheter wall.

* * * * *